(12) United States Patent
Sun et al.

(10) Patent No.: US 7,134,787 B2
(45) Date of Patent: Nov. 14, 2006

(54) METHOD OF CT BEAM HARDENING CALIBRATION

(75) Inventors: Haining Sun, Shenyang (CN); Shanshan Lou, Shenyang (CN); Jinjun Liu, Shenyang (CN)

(73) Assignee: Philips and Neusoft Medical Systems Co., Shenyang (CN)

( * ) Notice: Subject to any disclaimer, the term of this patent is extended or adjusted under 35 U.S.C. 154(b) by 247 days.

(21) Appl. No.: 10/868,170

(22) Filed: Jun. 15, 2004

(65) Prior Publication Data

US 2005/0013414 A1    Jan. 20, 2005

(30) Foreign Application Priority Data

Jul. 16, 2003 (CN) .................................. 03133763

(51) Int. Cl.
*G01D 18/00* (2006.01)
(52) U.S. Cl. .................................................... 378/207
(58) Field of Classification Search ............... 378/207, 378/18, 250, 505.1, 16, 145, 9, 901
See application file for complete search history.

(56) References Cited

U.S. PATENT DOCUMENTS

| | | | | |
|---|---|---|---|---|
| 4,288,695 | A * | 9/1981 | Walters et al. ................... | 378/5 |
| 5,953,444 | A * | 9/1999 | Joseph et al. ................. | 382/131 |
| 6,324,240 | B1 | 11/2001 | Yan et al. ........................ | 378/4 |
| 6,600,801 | B1 | 7/2003 | Raupach ......................... | 378/4 |
| 2004/0196960 | A1 * | 10/2004 | Tanigawa et al. ........... | 378/207 |
| 2004/0228451 | A1 * | 11/2004 | Wu et al. .................... | 378/207 |

OTHER PUBLICATIONS

J. Hsieh, "Computed Tomography: Principles, Design, Artifacts, and Recent Advances," *SPIE Press*, pp. 167-238, 2002.
C. H. Yan and R. T. Whalen, "Modeling of polychromatic attenuation using computed tomography reconstructed images," *Med. Phys.*, vol. 26, No. 4, pp. 631-642, 1999.
P. M. Joseph and C. Ruth, "A method for simultaneous correction of spectrum hardening artifacts in CT images containing both bone and iodine," *Med. Phys.*, vol. 24, No. 10, pp. 1629-1634, 1997.

* cited by examiner

*Primary Examiner*—Courtney Thomas
*Assistant Examiner*—Alexander Taningco
(74) *Attorney, Agent, or Firm*—Patterson, Thuente, Skaar & Christensen, P.A.

(57) ABSTRACT

A method of CT beam hardening calibration comprises: the step of obtaining raw data of a first phantom and a second phantom by scanning the first phantom and the second phantom respectively; the step of calculating a first filter material length and a second filter material length according to one ore more spectrum function and the raw data of the first phantom as well as the second phantom; the step of adjusting said spectrum function to make the first filter material length and the second filter material length agree with predefined conditions; the step of calculating a beam hardening curve according to the adjusted spectrum function and the first filter material length as well as the second filter material length met with the predefined conditions; and the step of processing the raw data by the calculated beam hardening curve to eliminate beam hardening effects. After calibrating raw data by using the adjusted spectrum curve, image results showed that artifacts such as shading dark artifacts and rings artifacts were significantly reduced.

9 Claims, 4 Drawing Sheets

METHOD OF CT BEAM HARDENING CALIBRATION

RELATED APPLICATION

This application claims priority to Chinese Application No. 03133763.5 filed Jul. 16, 2003.

FIELD OF THE INVENTION

This invention relates to the field of computed tomography (CT), especially to a method of CT beam hardening calibration that can eliminate the effects of nonlinear factors unrelated to the detected object that is subject to imaging.

BACKGROUND OF THE INVENTION

A CT tube emits x-rays, which is received by one or more detectors facing the tube. The detectors measure an attenuation value of X-rays between the CT tube and the detectors and calculate a distribution of material according to the attenuation value of a detected object measured from every angle of view as well as in coordination with a reconstruction program. Thus images can be reconstructed by the CT system.

Computed tomography reconstruction theory assumes that X-rays emitted from the tube are monochromatic, but this assumption is not the case in a typical system. In fact, the X-rays emitted from a typical system are polychromatic. Therefore, many dark artifacts can appear in reconstructed images obtained by a reconstruction program when an assumption of a monochromatic spectrum is made. These artifacts are referred as beam hardening artifacts. The program used to eliminate these artifacts is referred to as a beam hardening calibration program.

Beam hardening calibration has been the subject of much research around the world. Calibration programs can be divided into two categories according to processing mode: pre-processing and post-processing. Compared with pre-processing calibration methods, post-processing methods for calibration algorithms are more time consuming than pre-processing calibration methods and may cause image information losses, yet there are many post-processing methods emerging in international literature. Pre-processing methods are preferred due to their time-conserving qualities.

The common approach of a pre-processing method includes calculating a beam hardening curve by scanning one or more some special phantoms based upon existing theoretical equations as well as spectrum functions (SF), adjusting the raw data according to this beam hardening curve, and finishing with the beam hardening calibration. During processing, the selection of SF plays an important role on the beam hardening result. The program generally requires two assumptions: (1) that the attenuation detected by the detector in an ideal system should be equal to that of the detected object; and (2) in the ideal system, the X-ray beam emitted from the tube in an optic plane is uniformly distributed for different channels.

For the first assumption, the attenuation detected by the detector in an ideal system should be equal to that of the detected object. In an actual system, the X-ray it will pass through many unknown filter materials before the X-ray arrives at the detector, resulting in the change of beam spectrum. Beam hardening calibration performed according to the spectrum functions (SF) provided by the tube manufacturer may not yield desirable results.

For the second assumption, in an ideal system, the X-ray beam emitted by the tube in an optic plane is uniformly distributed for different channels. Former calibration programs are subject to this assumption and thus deploy consistent calibration parameters (e.g. spectrum function) for different channels during the calibration process. The rays emitted from the tube in an actual system are not uniformly distributed. Thus the attenuation materials that the X-ray beam pass through before arriving at the detected object are also different for different channels, resulting in artifacts if the same beam hardening calibration program is deployed for different channels.

Spectrum functions are an attribute of the tube, thus different tubes correspond to different spectrums. In addition, different scanning parameters correspond to different spectrums. The rays emitted from the tube that pass through a series of filter materials have been changed when they arrive at the detected object. For a different tube, SF is also different for different channels. So SF needs to be adjusted according to real situations.

FIG. 1 shows an example of a prior art system. X-rays emitted from tube 10 pass through filter materials 11-1–11-8 to detector 14. As shown in FIG. 1, SF provided by the tube manufacturer will be altered after it passes through a series of filter materials such as those illustrated by tube target 11-1, glass and metal beryllium of tube export window 11-2, insulating oil 11-3 used to immerse the tube, attached glass layer 11-4, a layer of tungsten on the inner side of the glass sealing 11-5, a first unit for controlling beam width 11-6, a first unit for controlling beam intensity 11-7, attached aluminum and molybdenum 11-8, and others. In addition, the altered SF arrives at the detector only after it passes through the second unit for controlling beam width 13 after passing through detected object 12. Thus, the information detected by the detector 14 includes that of all filter materials 11-1–11-8.

SUMMARY OF THE INVENTION

In view of the deficiencies existing in the current technologies, this invention presents a method of CT beam hardening calibration that includes obtaining raw data of a first phantom and a second phantom by scanning the first phantom and the second phantom respectively, calculating a first filter material length and a second filter material length according to any spectrum function and the raw data of the first phantom as well as the second phantom, adjusting the spectrum function to make the first filter material length and the second filter material length meet with predefined conditions, calculating a beam hardening curve according to the adjusted spectrum function and the first filter material length and the second filter material length having met the predefined conditions, and processing the raw data by the calculated beam hardening curve to eliminate beam hardening effects. The method of CT beam hardening calibration in the invention can eliminate the effects of filter material on CT imaging, and can perform beam hardening calibration on beams according to actual SF.

DETAILED DESCRIPTION OF THE PREFERRED EMBODIMENTS

The theory and implementation of the invention will be described in detail by referring to the figures herein.

Figure 1:
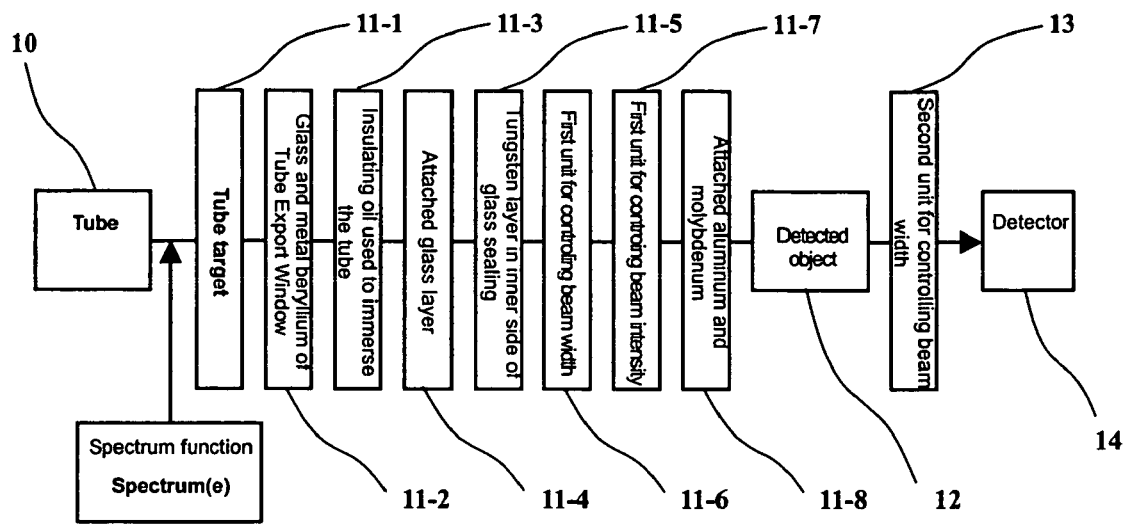
FIG. 1 illustrates an example of a prior art system using filter material through which X-rays generally pass from an X-ray tube to a detector.
Figure 2:
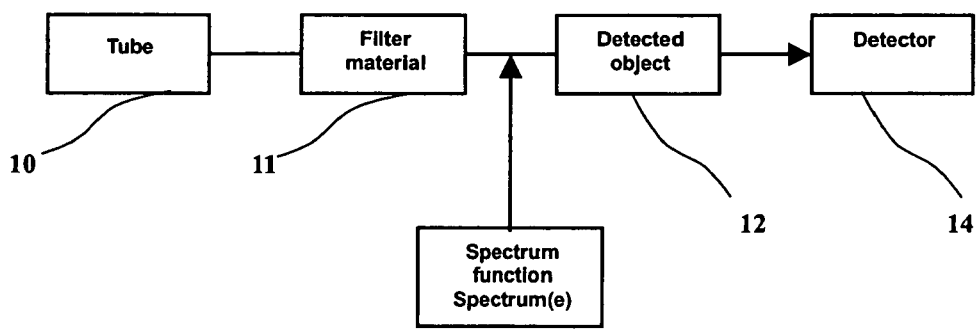
FIG. 2 is an illustration of an adaptation of FIG. 1 wherein the filter material has been simplified.

As described above, due to the effects of other filter materials, calibrating directly according to the spectrum functions provided by a tube manufacturer, desirable results are not obtained. Thus, the effects of filter materials must be considered during SF calculation. But if all filter materials are considered separately, the problem is complex to solve and remains indefinite. Hence, a simplification is made of filter materials 11 (i.e. regarding all the filter materials passed through as a black box), and calculations of the SF are made before arriving at the detected object 12, while neglecting the second unit for controlling beam width 13. As shown in the adaptation illustrated in FIG. 2, X-rays pass through the filter materials 11 and detected object 12 from tube 10 to detector 14, with the SF having direct action on the detected object 12 is an SF Spectrum(e) provided by a manufacturer of tube 10.

The following equation (1) gives an example of a relationship between data detected by the detector 14, the filter material 11 and the detected object 12. By discretizing equation (1), SF and the filter material can be determined based on raw data obtained by the detector 14 and phantom theory.

$$\exp(-Raw(n, w)) = \frac{\int \text{Spectrum}(n, e) \exp^{\mu_{Phantom}(e) Len_{Phantom}(n,w)} \exp^{\mu_{Filter}(e) Len_{Filter}(n,w)} de}{\int \text{Spectrum}(n, e) \exp^{\mu_{Filter}(e) Len_{Filter}(n,w)} de} \quad (1)$$

where $Raw(n,w)$ denotes raw data for the $n^{th}$ channel when a phantom w is scanned. $Spectrum(n,e)$ denotes a spectrum function of the $n^{th}$ channel. The value $\mu_{Phantom}(e)$ denotes an attenuation of the phantom. The value $Len_{Phantom}(n,w)$ denotes a length (distance) of phantom on the $n^{th}$ channel when Phantom w is scanned. The value $\mu_{Filter}(e)$ denotes an attenuation of filter material. The value $Len_{Filter}(n,w)$ denotes a length of filter material on the $n^{th}$ channel when Phantom w is scanned.

For certain channels, the relationship between SF Spectrum(n,e) and the length of the filter material $Len_{Filter}(n,w)$ is the characteristic of CT system and is generally unrelated to the object detected. The SF obtained according to equation (1) is related to filter material and the phantom length $Len_{phantom}(n,w)$. In another embodiment, to obtain SF unrelated to the phantom length, modification is made to the initial SF equation in (1) by using equation (2):

$$\text{Spectrum}(n,e) = \text{Spectrum}_{Initial}(n,e) \times (\text{AdjustS}(e))^{X(n)} \quad (2)$$

where $\text{Spectrum}_{Initial}(n,e)$ is an initial spectrum function, and AdjustS(e) is a spectrum adjusting function, which adopts the phantom attenuation function in actual deployment, and X(n) is an adjusting parameter. Two different phantoms can be considered. Then two phantoms, i.e. one large and one small, are measured.

Two phantoms, referred to as w1 and w2, are measured, with w1 being larger than w2. Two sets of $Len_{Filter}(n,w)$ can be obtained according to equation (1), i.e. $Len_{Filter}(n,w1)$ and $Len_{Filter}(n,w2)$. When X(n)=0, $Spectrum(n,e)=Spectrum_{Initial}(n,e)$. If there exists an X(n) such that $Len_{Filter}(n,w1) = Len_{Filter}(n,w2)$, the SF obtained according to equation (2) is unrelated to the detected phantom.

Typically, $Len_{Filter}(n,w1) - Len_{Filter}(n,w2)$ is monotonic and inversely proportional to the adjusting parameter X(n), which can be expressed by the following equation (3):

$$(Len_{Filter}(n,w1) - Len_{Filter}(n,w2)) \propto (X(n))^{-1} \quad (3)$$

This monotonic relationship can be used to adjust the spectrum and to obtain the final spectrum functions Spectrum(n,e) and filter material lengths $Len_{Filter}(n,w)$ simultaneously.

The adjusted SF Spectrum(n,e) and the filter material length $Len_{Filter}(n,w)$ of each channel are obtained. The beam hardening calibration curves of different attenuation materials are calculated according to equation (1), which are used to reduce the beam hardening effect.

Figure 3:
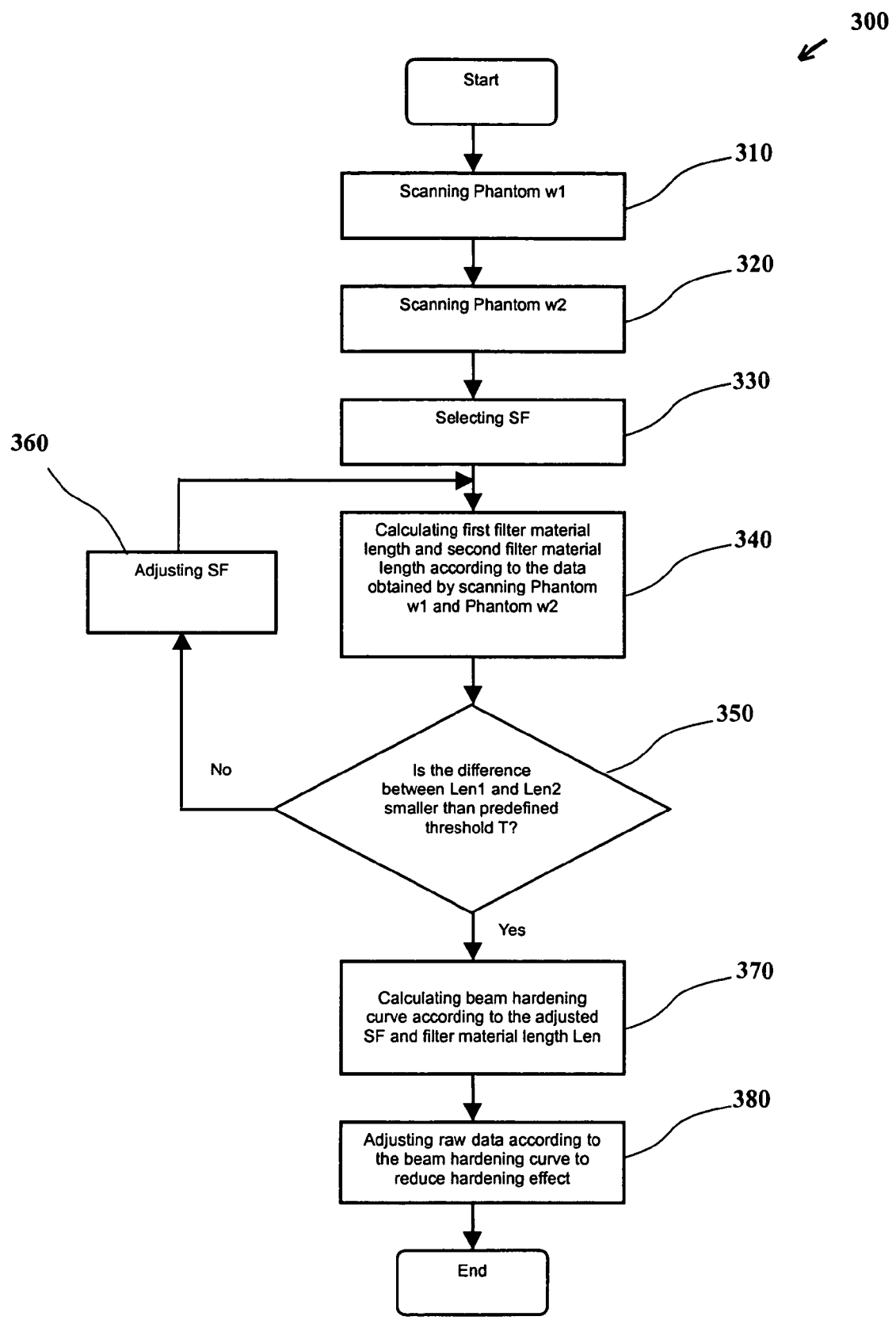
FIG. 3 is an embodiment of a beam hardening calibration method of the invention.

FIG. 3 shows an embodiment of a beam hardening calibration method of the invention.

As shown in FIG. 3, the method begins wherein the Phantom w1 with regular algebra shape is placed within the scanning region of a CT system at step 310, and the Phantom w1 is scanned. The slice thickness is selected, and the scanning mode is selected. Scanned raw data of Phantom w1, denoted by Raw(n, w1), is obtained.

After the scanned raw data of Phantom w1 is obtained, Phantom w1 is converted to Phantom w2 at step 320, and scanned raw data of w2 Raw(n, w2) is obtained. The same scanning mode using Phantom w1 is used to scan the Phantom w2 to obtain corresponding raw data. In step 330, an initial value $Spectrum_{Initial}(n,e)$ is randomly selected from an SF library provided by the X-ray tube manufacturer to comply with the scanning condition as the spectrum function Spectrum(n,e). In step 340, the scanned raw data Raw(n,w1) and Raw(n,w2) of Phantom w1 and Phantom w2 obtained in steps S1 and S2 respectively and as the initial value of SF Spectrum(n,e) obtained in step 330 are applied to into the equation (1). Equation (1) is solved to obtain the filter material length $Len_{Filter}(n,w1)$ and $Len_{Filter}(n,w2)$ for each channel, denoted as Len1 and Len2, respectively.

In step 350, if the difference between a plurality of calculated filter material lengths, i.e. Len1 and Len2, is less than the predefined threshold T, the following equation (4) will be true:

$$|Len1 - Len2| < T \quad (4)$$

where the threshold T is a predefined value such as. 0.001.

If the result obtained from step 350 indicates that the difference between a plurality of filter material lengths is equal to or larger than the predefined threshold T, Spectrum (n,e) can be adjusted according to equation (5) in step 360 with the predefined spectrum adjusting function AdjustS(e) and adjusting parameter X(n):

$$\text{Spectrum}(n,e) = \text{Spectrum}_{Initial}(n,e) \times (\text{AdjustS}(e))^{X(n)}$$

$$X(n)_{new}=X(n)_{old}/2, \text{Len}_{Filter}(n,w1)-\text{Len}_{Filter}(n,w2)>0 \quad (5)$$

$$X(n)_{new}=X(n)_{old}*2, \text{Len}_{Filter}(n,w1)-\text{Len}_{Filter}(n,w2)<0$$

In another embodiment of the adjustment of Spectrum(n, e), the SF Spectrum(n,e) can be tuned downward when the filter material length calculated for the larger Phantom w1 is longer than that calculated for the smaller Phantom w2, as shown in equation (5) setting $X(n)_{new}=X(n)_{old}/2$. In another embodiment; the SF can be tuned upward, e.g. setting $X(n)_{new}=X(n)_{old}*2$. After obtaining the adjusted SF Spectrum(n,e), the procedure returns to step 340.

If the result in step 350 indicates that the difference between the plurality of filter material lengths is smaller than the predefined threshold T, the plurality of filter material lengths can be regarded as equal, thus obtaining the filter material length Len. In another example embodiment, the mean between the plurality of filter material lengths can be assigned to Len. In step 370, a beam hardening curve can be calculated according to current SF and current filter material length Len and with equation (1) for each channel.

After a beam hardening curve is obtained in step 370, the raw data obtained in actual application is adjusted according to the beam hardening curve in step 380 to reduce the hardening effect.

In this embodiment, the method of determining whether the difference between filter material lengths is less than a predefined threshold is applied to determine if current SF meets with predetermined conditions.

In another embodiment of the invention, all steps outlined in FIG. 3 remain the same except for step 350. In step 350, determination is made whether to adjust SF by evaluating a ratio between two values within a predefined scope, as shown in equation (6):

$$t1 < |\text{Len}1/\text{Len}2 < t2 \quad (6)$$

Where t1 is slightly smaller than 1, for example 0.995; and t2 is slightly larger than 1, for example 1.005.

Similarly, the SF Spectrum(n,e) can be tuned down when the filter material length calculated for the larger Phantom w1 is longer than that calculated for the smaller Phantom w2, as shown in equation (5), thus setting $X(n)_{new}=X(n)_{old}/2$. Otherwise, the SF can be tuned up, for example setting $X(n)_{new}=X(n)_{old}*2$. After obtaining the adjusted SF Spectrum(n,e), the procedure returns to step S4.

Figure 4A:
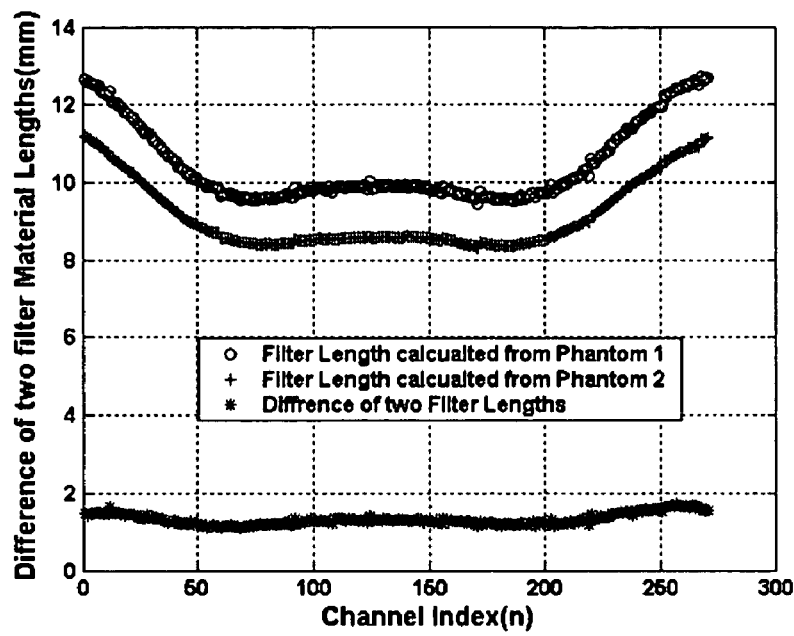
FIGS. 4(a) and 4(b) illustrate a comparison between initial filter material length and adjusted filter material length for a given channel applying the method of the invention.
Figure 4B:
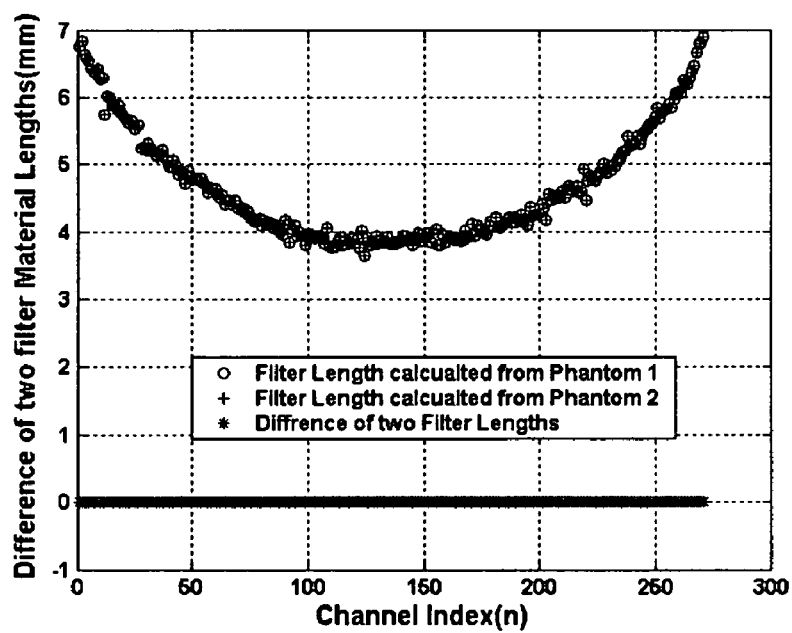

FIG. 4(*a*) plots the two filter lengths calculated according to two different filter phantoms, where a first line denoted by "o" indicates a curve of filter material length Len1 of phantom 1, a second line denoted by "+" indicates a curve of filter material length Len2 of phantom 2, and a third line denoted by "*" indicates the difference between the first and second lines. FIG. 4(*a*) illustrates the distinction between two filter material lengths at the beginning of the iteration.

FIG. 4(*b*) illustrates a relation between two filter material lengths after 20 iterations, as contrasted from those shown in FIG. 4(*a*). After 20 iterations, the two filter material lengths are substantially equal.

Figure 5:
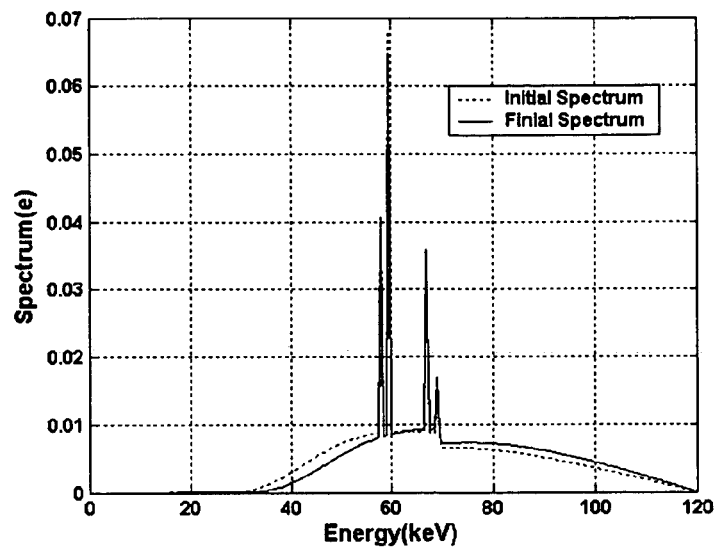
FIG. 5 illustrates a comparison between initial spectrum function and adjusted spectrum function.

FIG. 5 shows a comparison between an initial SF and an adjusted SF, where the dashed line indicates the initial SF and the solid line indicates an SF obtained after 20 iterations. In certain embodiments, for different channels, the initial SF and final SF may be different.

Figure 6:
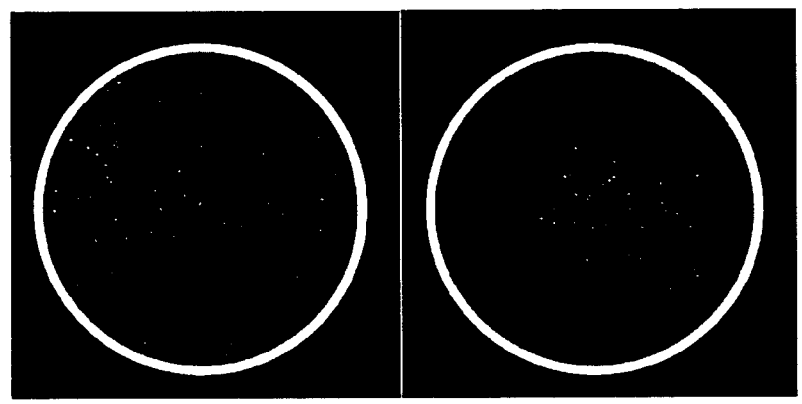
FIG. 6 illustrates a comparison of images before and after beam hardening calibration is performed with the method of the invention.
Figure 6:
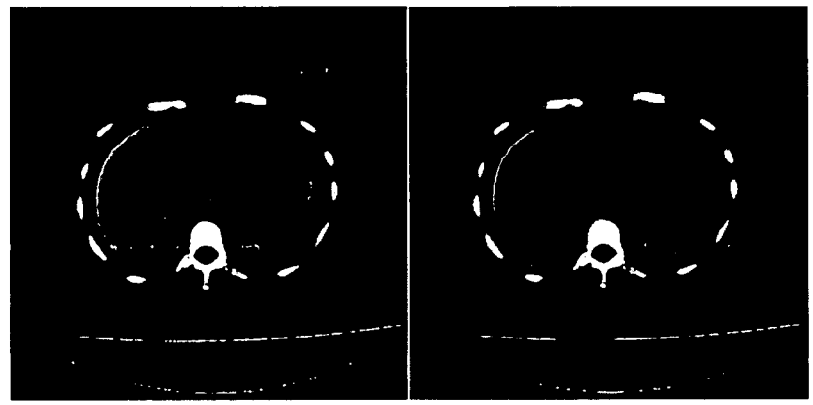

FIGS. 6(*a*) and 6(*b*) illustrate the comparison between an initial image and a calibrated image obtained when a beam hardening calibration method in the invention is applied. FIG. 6 illustrates the effectiveness of the beam hardening calibration method of the invention in reducing the beam hardening effect upon images.

During deployment, the method can be implemented by software or in the combination of hardware and software, such as a personal computer, workstation or digital signal processor (DSP) and others. These implementation methods are obvious for all those skilled in the field, which are presented here only for the purpose of explicit explanation but not to limit the invention.

Although this invention has been explained in the form of embodiments, these embodiments are only illustrative. Thus, according to above detailed description, many variations, modifications, and changes are all encompassed in interpretations by those skilled in the art. Those skilled in the art can modify the method in this invention while not exceeding the scope limited by the claims attached.

What is claimed is:

1. A method of CT beam hardening calibration comprising:
    a step of obtaining raw data of a first phantom and a second phantom by scanning the first phantom and the second phantom respectively;
    a step of calculating a first filter material length and a second filter material length according to one or more spectrum functions and the raw data of the first phantom and the second phantom;
    a step of adjusting the spectrum function to make the first filter material length and the second filter material length agree with predefined conditions;
    a step of calculating a beam hardening curve according to the adjusted spectrum function and the first filter material length as well as the second filter material length met with the predefined conditions;
    a step of processing the raw data by the calculated beam hardening curve to eliminate beam hardening effects;
    wherein the step of adjusting the spectrum function to make the first filter material length and the second filter material length meet with predefined conditions comprises:
    judging if an absolute value of the difference between the first filter material length and the second filter material length is less than a predefined threshold; and
    adjusting the spectrum function according to following equation if the judging result is negative:

$$\text{Spectrum}(n,e)=\text{Spectrum}_{Initial}(n,e) \times (\text{AdjustS}(e))^{X(n)}$$

where $\text{Spectrum}_{Initial}(n,e)$ is an initial spectrum function; AdjustS(e) is a spectrum adjusting function; and X(n) is an adjusting parameter.

2. The method of CT beam hardening calibration of claim 1, wherein the first filter material length and second filter material length are calculated according to following equation:

$$\exp(-Raw(n,w)) = \frac{\int \text{Spectrum}(n,e)\exp^{\mu_{Phantom}(e)\text{Len}_{Phantom}(n,w)} \exp^{\mu_{Filter}(e)\text{Len}_{Filter}(n,w)} de}{\int \text{Spectrum}(n,e)\exp^{\mu_{Filter}(e)\text{Len}_{Filter}(n,w)} de}$$

where Raw(n,w) denotes raw data for the $n^{th}$ channel when a phantom w is scanned; Spectrum(n,e) denotes a spectrum function the $n^{th}$ channel; $\mu_{Phantom}(e)$ denotes an attenuation of the phantom; $\text{Len}_{Phantom}(n,w)$ denotes a length of the phantom on the $n^{th}$ channel when the phantom w is scanned; $\mu_{Filter}(e)$ denotes an attenuation of filter material; and $Len_{Filter}(n,w)$ denotes a length of filter material on the $n^{th}$ channel when the phantom w is scanned.

3. The method of CT beam hardening calibration of claim 1, wherein the difference between the first filter material length and the second filter material length is monotonic and inversely proportional to the adjusting parameter $X(n)$.

4. The method of CT beam hardening calibration of claim 1, wherein the spectrum adjusting function is a phantom attenuation function.

5. The method of CT beam hardening calibration of claim 1, wherein when the filter material length obtained with the larger one of the first phantom and second phantom is longer than the other filter material length, tuning down the adjusting parameter; otherwise, tuning up the adjusting parameter.

6. A method of CT beam hardening calibration comprising:
   a step of obtaining raw data of a first phantom and a second phantom by scanning the first phantom and the second phantom respectively;
   a step of calculating a first filter material length and a second filter material length according to one or more spectrum functions and the raw data of the first phantom and the second phantom;
   a step of adjusting the spectrum function to make the first filter material length and the second filter material length agree with predefined conditions;
   a step of calculating a beam hardening curve according to the adjusted spectrum function and the first filter material length as well as the second filter material length met with the predefined conditions;
   a step of processing the raw data by the calculated beam hardening curve to eliminate beam hardening effects;
   wherein the step of adjusting the spectrum function to make the first filter material length and the second filter material length meet with predefined conditions comprises:
   judging if an absolute value of the ratio between the first filter material length and the second filter material length is within a predefined scope; and
   adjusting the spectrum function according to following equation if above judging result is negative:

$$Spectrum(n,e) = Spectrum_{Initial}(n,e) \times (AdjustS(e))^{X(n)}$$

where $Spectrum_{Initial}(n,e)$ is an initial spectrum function; $AdjustS(e)$ is a spectrum adjusting function; and $X(n)$ is an adjusting parameter.

7. The method of CT beam hardening calibration of claim 6, wherein the difference between the first filter material length and the second filter material length is monotonic and inversely proportional to the adjusting parameter $X(n)$.

8. The method of CT beam hardening calibration of claim 6, wherein the spectrum adjusting function is a phantom attenuation function.

9. The method of CT beam hardening calibration of claim 6, wherein when the filter material length obtained with the larger one of the first phantom and second phantom is longer than the other filter material length, tuning down the adjusting parameter; otherwise, tuning up the adjusting parameter.

* * * * *